(12) United States Patent
Noda et al.

(10) Patent No.: US 10,494,595 B2
(45) Date of Patent: Dec. 3, 2019

(54) METHOD FOR PRODUCING CONTAINER FOR FORMING EMBRYOID BODY

(71) Applicant: NOF CORPORATION, Tokyo (JP)

(72) Inventors: Tomozumi Noda, Kawasaki (JP);
Fumio Nakashima, Kawasaki (JP);
Satoshi Yamada, Kawasaki (JP);
Nobuyuki Sakamoto, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 138 days.

(21) Appl. No.: 15/523,698

(22) PCT Filed: Oct. 30, 2015

(86) PCT No.: PCT/JP2015/080837
§ 371 (c)(1),
(2) Date: May 2, 2017

(87) PCT Pub. No.: WO2016/072369
PCT Pub. Date: May 12, 2016

(65) Prior Publication Data
US 2017/0335266 A1    Nov. 23, 2017

(30) Foreign Application Priority Data
Nov. 4, 2014 (JP) .................... 2014-224752

(51) Int. Cl.
*C12M 1/00*    (2006.01)
*B05D 7/22*    (2006.01)
*C12M 3/00*    (2006.01)

(52) U.S. Cl.
CPC ............. *C12M 23/20* (2013.01); *B05D 7/22* (2013.01); *C12M 21/08* (2013.01)

(58) Field of Classification Search
CPC ......... C12N 5/08; C12N 5/0603; C12M 23/20
USPC ................................. 435/289.1, 366
See application file for complete search history.

(56) References Cited

U.S. PATENT DOCUMENTS

2006/0252148 A1* 11/2006 Kurosawa ............ C12N 5/0603
435/366
2014/0011269 A1*  1/2014 Sakura .................. C12M 21/06
435/289.1

OTHER PUBLICATIONS

PCT International Search Report dated Jan. 26, 2016 in connection with PCT International Application No. PCT/JP2015/080837, 4 pages.

* cited by examiner

*Primary Examiner* — Dah-Wei D. Yuan
*Assistant Examiner* — Andrew J Bowman
(74) *Attorney, Agent, or Firm* — Amster, Rothstein & Ebenstein LLP

(57) ABSTRACT

An object is to provide a method of manufacturing a vessel for embryoid body formation excellent in formability of an embryoid body and suitable for optical observation.

18 Claims, 1 Drawing Sheet

[Fig.1]
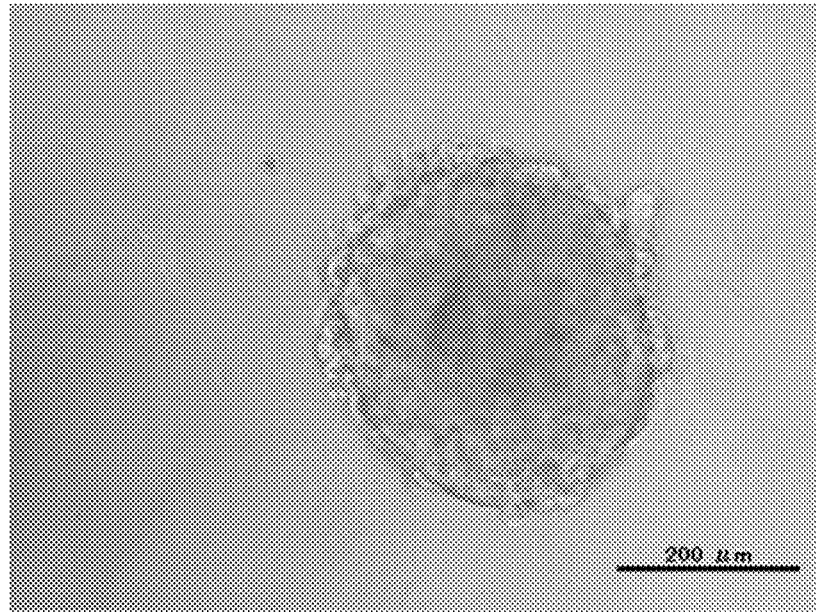
[Fig.2]
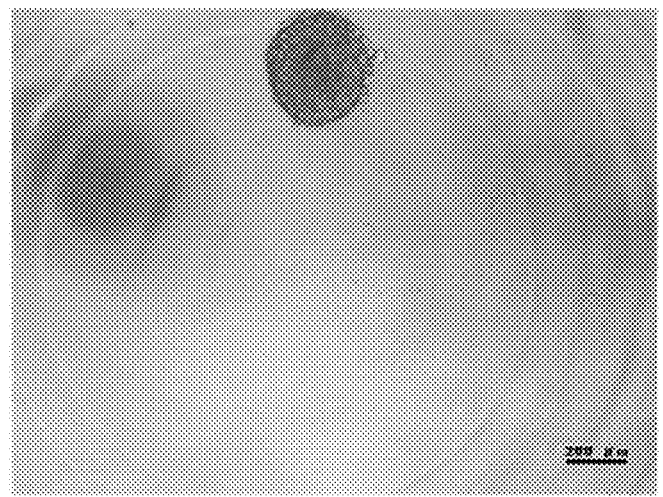

US 10,494,595 B2

METHOD FOR PRODUCING CONTAINER FOR FORMING EMBRYOID BODY

CROSS-REFERENCE TO RELATED APPLICATIONS

This application is a U.S. national stage entry under 35 U.S.C. § 371 of PCT International Patent Application No. PCT/JP2015/080837, filed Oct. 30, 2015, which claims priority to Japanese Patent Application No. 2014-224752, filed Nov. 4, 2014, the contents of which are incorporated by reference herein into the subject application.

TECHNICAL FIELD

The present invention relates to a method of manufacturing a vessel for embryoid body formation for use in forming an embryoid body.

The present application claims priority from Japanese Patent Application No. 2014-224752, which is incorporated herein by reference.

BACKGROUND ART

Stem cells, such as embryonic stem cells and somatic stem cells, are capable of differentiating into various types of cells in vitro. As a method of differentiating stem cells in vitro, there is utilized a method involving subjecting stem cells to floating culture to form pseudo-embryos, called embryoid bodies, or a method involving coculturing cells, such as stromal cells, that support differentiation and proliferation, with stem cells. Of those, floating culture is the most common method of differentiating stem cells in vitro. For example, when mouse embryonic stem cells are subjected to floating culture in a culture vessel, for example, a petri dish, without leukemia inhibitory factor (LIF) so as not to adhere to the vessel, cell aggregates are formed. The cell aggregates formed by floating culture are called embryoid bodies (EB). It is known that the resultant cell aggregates differentiate into various types of cells thereafter.

The embryoid body (EB) has a ball-like structure formed of a bilayer of cells. The outer layer corresponds to visceral endoderm, and the inner layer corresponds to embryonic ectoderm. The two endoderms are separated by a basement membrane. The structure of the embryoid body is quite similar to that of a cylindrical embryo, which is a day 6 mouse embryo. As far as this similarity is concerned, the structure resembles the normal stage of embryogenesis. In embryoid bodies, mesoderm is also induced, and cardiomyocytes, blood cells, and even primitive vascular networks are developed. In addition, when plated on a culture petri dish and cultured further, the embryoid bodies differentiate into various types of cells, including, for example, neurons, keratinocytes, chondrocytes, and adipocytes. It has recently been confirmed that the cells that differentiate via formation of embryoid bodies are differentiated not only into somatic cells, but also into a germ cell lineage. For utilizing pluripotency of stem cells, it is suitable that the embryoid bodies be formed.

In general, as a technology for forming cell aggregates, there are known a hanging drop method involving culturing cells in hanging drops, and a rotary culture method or a centrifugal method disclosed in Non Patent Literature 1. However, in each of those methods, setting of culture conditions is complicated.

In Patent Literature 1, as a vessel for forming cell aggregates, there is disclosed a culture vessel formed of polyhydroxylethyl methacrylate, an ethylene-vinyl alcohol copolymer, or the like.

In addition, in Patent Literature 2, there is disclosed a method involving subjecting ES cells, which are one type of stem cells, to floating culture to form embryoid bodies. In the method of forming embryoid bodies of Patent Literature 2, a vessel for embryoid body formation coated with a polymer having a phosphorylcholine-like group is used. In Patent Literature 2, there is disclosed a method of coating the vessel for embryoid body formation with the polymer, but detailed investigations are not conducted.

CITATION LIST

Patent Literature

[PTL 1] JP 06-327462 A
[PTL 2] WO 2005/001019 A1

Non Patent Literature

[NPL 1] Biotechnol. J. 2008, 3, 1172-1184

SUMMARY OF INVENTION

Technical Problem

A vessel for embryoid body formation coated with a polymer having a phosphorylcholine-like group has a problem in that a variation in cell adhesion property occurs owing to coating nonuniformity, and a problem in that when the coating film has a large thickness, a pattern of the coating film occurs on the vessel, with the result that the pattern appears in a background at the time of microscopic observation for, for example, confirming formation of embryoid bodies. That is, the vessel for embryoid body formation coated with a polymer having a phosphorylcholine-like group has problems in embryoid body formation and optical observation of cells that differentiate from embryoid bodies. It is an object of the present invention to solve the problems of the related-art vessel for embryoid body formation. Accordingly, it is an object of the present invention is to provide a method of manufacturing a vessel for embryoid body formation excellent in formability of an embryoid body and suitable for optical observation.

Solution to Problem

The inventors of the present invention have found that a vessel for embryoid body formation allowing efficient formation of an embryoid body and being excellent in optical observability can be manufactured through the following two steps: applying a specific amount of a compound having, in a side chain thereof, a phosphorylcholine-like group onto an inner surface of a vessel, followed by drying to form a coating film; and then leveling the coating film with a specific amount of a treatment liquid. Thus, the present invention has been completed.

That is, the present invention includes the following.

1. A method of manufacturing a vessel for embryoid body formation for use in floating culture of stem cells to form an embryoid body, the method including:

a step (A) of coating an inner surface of a vessel defining a region for floating culture of stem cells with an alcohol-based medium solution having mixed therein a compound having, in a side chain thereof, a phosphorylcholine-like group represented by the formula (1) so that an amount of the compound having, in the side chain thereof, the phosphorylcholine-like group is from 0.1 mg/cm$^2$ to 10 mg/cm$^2$, followed by drying; and a step (B) of adding, to a coating film on the inner surface of the vessel produced in the step (A), a water/alcohol-based medium solution at from 15 mg/cm$^2$ to 150 mg/cm$^2$ to swell the coating film, followed by drying:

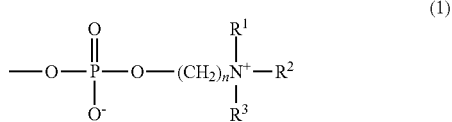
(1)

where R$^1$, R$^2$, and R$^3$ are identical or different groups, and each represent a hydrogen atom, or an alkyl group or hydroxyalkyl group having 1 to 6 carbon atoms, and n represents an integer of from 1 to 4.

2. A method of manufacturing a vessel for embryoid body formation according to the above-mentioned item 1, further including a step (C) of sterilizing the inner surface of the vessel with an ethylene oxide gas.

3. A method of manufacturing a vessel for embryoid body formation according to the above-mentioned item 1 or 2, in which the compound having, in the side chain thereof, the phosphorylcholine-like group includes at least one kind of a copolymer of a phosphorylcholine-like group-containing monomer (M) represented by the formula (2) and another monomer:

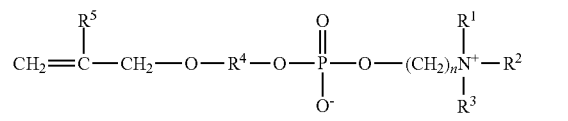
(2)

where R$^1$, R$^2$, and R$^3$ are identical or different groups, and each represent a hydrogen atom, or an alkyl group or hydroxyalkyl group having 1 to 6 carbon atoms, R$^4$ represents an alkyl group having 1 to 6 carbon atoms, R$^5$ represents a hydrogen atom or a methyl group, and n represents an integer of from 1 to 4.

4. A method of manufacturing a vessel for embryoid body formation according to the above-mentioned item 3, in which the another monomer contains an alkyl (meth)acrylate or glycidyl (meth)acrylate.

5. A method of manufacturing a vessel for embryoid body formation according to any one of the above-mentioned items 1 to 4, in which the compound having, in the side chain thereof, the phosphorylcholine-like group includes a copolymer of 2-methacryloyloxyethylphosphorylcholine, and butyl methacrylate, glycidyl methacrylate, and/or methacrylic acid.

6. A method of manufacturing a vessel for embryoid body formation according to any one of the above-mentioned items 1 to 5, in which the compound having, in the side chain thereof, the phosphorylcholine-like group includes a copolymer of 2-methacryloyloxyethylphosphorylcholine and butyl methacrylate.

7. A method of manufacturing a vessel for embryoid body formation according to the above-mentioned item 6, in which the copolymer has a molar ratio of 2-methacryloyloxyethylphosphorylcholine and butyl methacrylate of from 10 to 90:from 90 to 10.

8. A method of manufacturing a vessel for embryoid body formation according to any one of the above-mentioned items 1 to 5, in which the compound having, in the side chain thereof, the phosphorylcholine-like group includes a copolymer of 2-methacryloyloxyethylphosphorylcholine, butyl methacrylate, and methacrylic acid.

9. A vessel for embryoid body formation, which is manufactured by the method of manufacturing a vessel for embryoid body formation of any one of the above-mentioned items 1 to 8.

10. A method of forming an embryoid body through use of a vessel for embryoid body formation for use in floating culture of stem cells to form an embryoid body, the method including:

a step (D) of providing a vessel for embryoid body formation formed by:
a step (A) of coating an inner surface of a vessel defining a region for floating culture of stem cells with an alcohol-based medium solution having mixed therein a compound having, in a side chain thereof, a phosphorylcholine-like group represented by the formula (1) so that an amount of the compound having, in the side chain thereof, the phosphorylcholine-like group is from 0.1 mg/cm$^2$ to 10 mg/cm$^2$, followed by drying; and
a step (B) of adding, to a coating film on the inner surface of the vessel produced in the step (A), a water/alcohol-based medium solution at from 15 mg/cm$^2$ to 150 mg/cm$^2$ to swell the coating film, followed by drying; and
a step (E) of subjecting embryonic stem cells to floating culture in the vessel for embryoid body formation provided in the step (D):

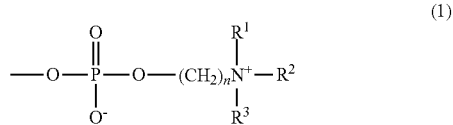
(1)

where R$^1$, R$^2$, and R$^3$ are identical or different groups, and each represent a hydrogen atom, or an alkyl group or hydroxyalkyl group having 1 to 6 carbon atoms, and n represents an integer of from 1 to 4.

11. A method of forming an embryoid body according to the above-mentioned item 10, further including, after the step (B), a step (C) of sterilizing the inner surface of the vessel with an ethylene oxide gas.

12. A method of forming an embryoid body according to the above-mentioned item 11 or 12, in which the compound having, in the side chain thereof, the phosphorylcholine-like group includes at least one kind of a copolymer of a phosphorylcholine-like group-containing monomer (M) represented by the formula (2) and another monomer:

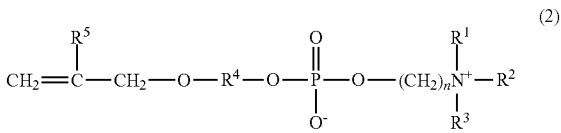
(2)

where $R^1$, $R^2$, and $R^3$ are identical or different groups, and each represent a hydrogen atom, or an alkyl group or hydroxyalkyl group having 1 to 6 carbon atoms, $R^4$ represents an alkyl group having 1 to 6 carbon atoms, $R^5$ represents a hydrogen atom or a methyl group, and n represents an integer of from 1 to 4.

13. A method of forming an embryoid body according to the above-mentioned item 12, in which the another monomer contains an alkyl (meth)acrylate or glycidyl (meth) acrylate.

14. A method of forming an embryoid body according to any one of the above-mentioned items 10 to 13, in which the compound having, in the side chain thereof, the phosphorylcholine-like group includes a copolymer of 2-methacryloyloxyethylphosphorylcholine, and butyl methacrylate, glycidyl methacrylate, and/or methacrylic acid.

15. A method of forming an embryoid body according to any one of the above-mentioned items 10 to 14, in which the compound having, in the side chain thereof, the phosphorylcholine-like group includes a copolymer of 2-methacryloyloxyethylphosphorylcholine and butyl methacrylate.

16. A method of forming an embryoid body according to the above-mentioned item 15, in which the copolymer has a molar ratio of 2-methacryloyloxyethylphosphorylcholine and butyl methacrylate of from 10 to 90:from 90 to 10.

17. A method of forming an embryoid body according to any one of the above-mentioned items 10 to 14, in which the compound having, in the side chain thereof, the phosphorylcholine-like group includes a copolymer of 2-methacryloyloxyethylphosphorylcholine, butyl methacrylate, and methacrylic acid.

Advantageous Effects of Invention

The method of manufacturing a vessel for embryoid body formation of the present invention can provide a vessel for embryoid body formation having a homogeneous vessel surface as compared to a related-art vessel. The vessel for embryoid body formation produced by the manufacturing method of the present invention is useful because the vessel is excellent in efficiency of embryoid body formation and excellent in optical observability.

BRIEF DESCRIPTION OF DRAWINGS

FIG. 1 is a photocopy of a phase contrast micrograph of an embryoid body formed through use of a vessel for embryoid body formation of Example 3.

FIG. 2 is a photocopy of a phase contrast micrograph of an embryoid body formed through use of a vessel for embryoid body formation of Comparative Example 3.

DESCRIPTION OF EMBODIMENTS

The present invention is directed to a method of manufacturing a vessel for embryoid body formation for use in floating culture of stem cells to form an embryoid body. In the present invention, the stem cells are cells capable of self-replicating and capable of differentiating into various types of cells (pluripotent). Examples of the stem cells include embryonic stem cells (ES cells), somatic stem cells, and induced pluripotent stem cells (iPS cells).

The method of manufacturing a vessel for embryoid body formation of the present invention includes the following step (A) and step (B).

The step (A) is a step of applying an alcohol-based medium solution having mixed (dissolved) therein a compound having, in a side chain thereof, a phosphorylcholine-like group represented by the following formula (1) (hereinafter referred to simply as "solution containing the compound having, in the side chain thereof, the phosphorylcholine-like group") onto an inner surface (inside surface) of a vessel defining a region for floating culture so that the amount of the compound is from 0.1 mg/cm² to 10 mg/cm², to thereby coat the inner surface of the vessel, followed by drying.

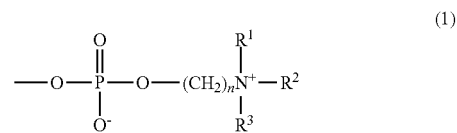

In the formula (1), $R^1$, $R^2$, and $R^3$ are identical or different groups, and each represent a hydrogen atom, or an alkyl group or hydroxyalkyl group having 1 to 6 carbon atoms, and n represents an integer of from 1 to 4.

Examples of the alkyl group having 1 to 6 carbon atoms include a methyl group, an ethyl group, a propyl group, a butyl group, a pentyl group, a hexyl group, a cyclohexyl group, and a phenyl group. Examples of the hydroxyalkyl group having 1 to 6 carbon atoms include a hydroxymethyl group, a 2-hydroxyethyl group, a 3-hydroxypropyl group, a 4-hydroxybutyl group, a 5-hydroxypentyl group, and a 6-hydroxyhexyl group.

Through the step (A), a coating film containing the compound having, in the side chain thereof, the phosphorylcholine-like group can be formed (a coating layer can be applied) onto a desired inner surface of the vessel, and a surface having the phosphorylcholine-like group can be formed on the inner surface of the vessel.

In the step (A), after the solution containing the compound having, in the side chain thereof, the phosphorylcholine-like group has been applied onto the desired inner surface of the vessel to coat the desired inner surface of the vessel, that is, after a solution layer formed of the solution has been formed on the desired inner surface of the vessel, the solution layer is dried. As means for coating the desired inner surface of the vessel with the solution containing the compound having, in the side chain thereof, the phosphorylcholine-like group, there is given, for example: means involving soaking the vessel in the solution containing the compound having, in the side chain thereof, the phosphorylcholine-like group, and pulling the vessel out of the solution; means involving adding or injecting the solution containing the compound having, in the side chain thereof, the phosphorylcholine-like group to the desired inner surface of the vessel; or means involving spraying the solution containing the compound having the phosphorylcholine-like group onto the desired inner surface of the vessel. Of those, means involving adding or injecting the solution containing the compound having, in the side chain thereof, the phosphorylcholine-like group to the desired inner surface of the vessel is preferred because the compound having, in the side chain thereof, the phosphorylcholine-like group can be reliably applied onto the desired inner surface of the vessel and the amount of coating of the solution can be adjusted. In addition, any means may be used as means for drying the inner surface of the vessel as long as the object of the present invention is not impaired.

As a condition for coating the desired inner surface of the vessel with the solution containing the compound having, in the side chain thereof, the phosphorylcholine-like group, the compound having, in the side chain thereof, the phosphorylcholine-like group is applied so that the amount thereof is from 0.1 mg to 10 mg (0.1 mg/cm² to 10 mg/cm²), preferably from 0.15 mg to 1 mg per 1 cm² of the inner surface of the vessel. When the amount of the compound having, in the side chain thereof, the phosphorylcholine-like group is less than 0.1 mg/cm², the coating becomes nonuniform, and the cells adhere onto the inner surface of the vessel, resulting in insufficient embryoid body formation. In addition, when the amount of the compound having, in the side chain thereof, the phosphorylcholine-like group is more than 10 mg/cm², coating nonuniformity occurs significantly, resulting in poor observability under a microscope. Further, such coating nonuniformity cannot be eliminated by leveling treatment to be performed after the step (A), and hence a pattern occurs on the surface. In addition, high raw material cost is required, and hence such amount is not practical.

The compound having, in the side chain thereof, the phosphorylcholine-like group represented by the formula (1) is preferably a polymer having the phosphorylcholine-like group represented by the formula (1), and may be any polymer having the phosphorylcholine-like group. The compound having, in the side chain thereof, the phosphorylcholine-like group represented by the formula (1) is, for example, preferably at least one kind of a homopolymer of a phosphorylcholine-like group-containing monomer (M) represented by the formula (2), or a copolymer of the monomer (M) and another monomer, more preferably at least one kind of a copolymer of the monomer (M) and another monomer.

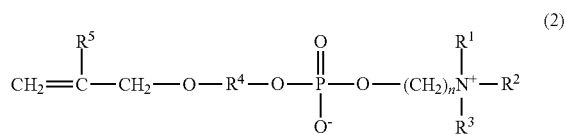

In the formula (2), $R^1$, $R^2$, $R^3$, and n are the same as those in the formula (1), $R^4$ represents an alkyl group having 1 to 6 carbon atoms, and $R^5$ represents a hydrogen atom or a methyl group. The definition of the alkyl group having 1 to 6 carbon atoms is the same as that in the formula (1).

Examples of the monomer (M) represented by the formula (2) include 2-((meth)acryloyloxy)ethyl-2'-(trimethylammonio)ethyl phosphate, 3-((meth)acryloyloxy)propyl-2'-(trimethylammonio)ethyl phosphate, 4-((meth)acryloyloxy)butyl-2'-(trimethylammonio)ethyl phosphate, 5-((meth)acryloyloxy) pentyl-2'-(trimethylammonio)ethyl phosphate, 6-((meth)acryloyloxy)hexyl-2'-(trimethylammonio)ethyl phosphate, 2-((meth)acryloyloxy)ethyl-2'-(triethylammonio)ethyl phosphate, 2-((meth)acryloyloxy)ethyl-2'-(tripropylammonio)ethyl phosphate, 2-((meth)acryloyloxy)ethyl-2'-(tributylammonio)ethyl phosphate, 2-((meth)acryloyloxy) ethyl-2'-(tricyclohexylammonio)ethyl phosphate, 2-((meth) acryloyloxy)ethyl-2'-(triphenylammonio)ethyl phosphate, 2-((meth)acryloyloxy)propyl-2'-(trimethylammonio)ethyl phosphate, 2-((meth)acryloyloxy)butyl-2'-(trimethylammonio)ethyl phosphate, 2-((meth)acryloyloxy) pentyl-2'-(trimethylammonio)ethyl phosphate, and 2-((meth)acryloyloxy) hexyl-2'-(trimethylammonio)ethyl phosphate.

Of those, as the monomer (M) represented by the formula (2), 2-((meth)acryloyloxy)ethyl-2'-(trimethylammonio)ethyl phosphate is preferred, and 2-(methacryloyloxy)ethyl-2'-(trimethylammonio)ethyl phosphate (also referred to as 2-methacryloyloxyethylphosphorylcholine; hereinafter abbreviated as MPC) is more preferred in terms of availability and preventing adhesion of stem cells to the vessel to allow expression of their ability to form embryoid bodies.

Examples of the another monomer for obtaining the copolymer include: hydrophobic monomers; hydroxy group-containing (meth)acrylates, such as 2-hydroxyethyl (meth)acrylate, 2-hydroxybutyl (meth)acrylate, and 4-hydroxybutyl (meth)acrylate; ionic group-containing monomers, such as acrylic acid, methacrylic acid, styrenesulfonic acid, (meth)acryloyloxyphosphonic acid, and 2-hydroxy-3-(meth)acryloyloxypropyltrimethylammonium chloride; nitrogen-containing monomers, such as (meth)acrylamide, aminoethyl methacrylate, and dimethylaminoethyl (meth) acrylate; polyethylene glycol (meth)acrylate; glycidyl (meth)acrylate; and a mixture of two or more kinds thereof.

Examples of the hydrophobic monomers include: straight or branched alkyl (meth)acrylates, such as methyl (meth) acrylate, ethyl (meth)acrylate, butyl (meth)acrylate, 2-ethylhexyl (meth)acrylate, lauryl (meth)acrylate, and stearyl (meth)acrylate; cyclic alkyl (meth)acrylates, such as cyclohexyl (meth)acrylate; aromatic (meth)acrylates, such as benzyl (meth)acrylate and phenoxyethyl (meth)acrylate; hydrophobic polyalkylene glycol (meth)acrylates, such as polypropylene glycol (meth)acrylate; styrene-based monomers, such as styrene, methylstyrene, and chloromethylstyrene; vinyl ether-based monomers, such as methyl vinyl ether and butyl vinyl ether; vinyl ester-based monomers, such as vinyl acetate and vinyl propionate; and a mixture of two or more kinds thereof.

In the copolymer, the content of a unit derived from the monomer (M) is 10 mol % or more and 90 mol % or less, preferably 30 mol % or more and 80 mol % or less in the units of the copolymer. When the content of the unit derived from the monomer (M) is 10 mol % or more and 90 mol % or less, the vessel surface can be coated with the phosphorylcholine-like group represented by the formula (1), and a sufficient effect of the coating is exhibited.

When the copolymer contains the hydrophobic monomer as the another monomer, the content of a unit derived from the hydrophobic monomer is preferably 90 mol % or less, particularly preferably from 20 mol % to 90 mol % in the units of the copolymer. A copolymer having the unit derived from the hydrophobic monomer has improved elution resistance. However, when the content of the unit derived from the hydrophobic monomer is more than 90 mol %, the amount of coating of the phosphorylcholine-like group represented by the formula (1) on the vessel surface is so small that a sufficient effect of the coating may not be exhibited. Accordingly, such content is not preferred.

The copolymer is given improved elution resistance when the copolymer contains a unit derived from a monomer other than the hydrophobic monomer as the another monomer. This allows use of a surfactant or an organic solvent in a medium or the like, which is preferred. For example, a copolymer using glycidyl (meth)acrylate as the another monomer other than the hydrophobic monomer may be reacted with, for example, an amino group or a carboxyl group on the vessel surface to chemically bond the copolymer to the desired surface. In the copolymer, the content of the unit derived from the another monomer other than the hydrophobic monomers is preferably 70 mol % or less.

The molecular weight of the homopolymer of the phosphorylcholine-like group-containing monomer (M) represented by the formula (2), or the copolymer of the monomer (M) and the another monomer is usually from 5,000 to 5,000,000 in weight average molecular weight. For effectively preventing adhesion of stem cells to the vessel to allow expression of their ability to form embryoid bodies, and improving the elution resistance of the polymer, the molecular weight of the polymer is preferably from 10,000 to 2,000,000. The weight average molecular weight may be measured by a method to be described later in Examples.

The alcohol-based medium solution containing the compound having, in the side chain thereof, the phosphorylcholine-like group may be any solution as long as the solution is obtained by mixing and dissolving the compound having, in the side chain thereof, the phosphorylcholine-like group in an alcohol-based solvent. The alcohol-based solvent is preferably a lower alcohol, and examples thereof include methanol, ethanol, and propanol, and a mixture thereof.

The compound having, in the side chain thereof, the phosphorylcholine-like group may be preferably exemplified by, but not particularly limited to:

a copolymer of 2-methacryloyloxyethylphosphorylcholine, and butyl methacrylate, glycidylmethacrylate, and/or methacrylic acid;

a copolymer of 2-methacryloyloxyethylphosphorylcholine and butyl methacrylate;

a copolymer of 2-methacryloyloxyethylphosphorylcholine and butyl methacrylate, in which the copolymer has a molar ratio of 2-methacryloyloxyethylphosphorylcholine and butyl methacrylate of from 10 to 90:from 90 to 10; and a copolymer of 2-methacryloyloxyethylphosphorylcholine, butyl methacrylate, and methacrylic acid.

The method of manufacturing a vessel for embryoid body formation of the present invention includes, after the step (A), the step (B) of applying, onto a coating film having unevenness or nonuniformity, which has been formed on the inner surface of the vessel, a water/alcohol-based medium solution to swell the coating film, followed by drying of the coating film. In the step (B), leveling treatment is performed by swelling the coating film formed in the step (A) with the water/alcohol-based medium solution and then drying the coating film again. The leveling treatment refers to treatment for smoothening and homogenizing the exposed surface of the coating film to allow the coating film to have a uniform film thickness, to thereby prevent formation of unevenness or nonuniformity. In the step (B), through use of the water/alcohol-based medium solution, the leveling treatment is performed by lowering the evaporation rate of the water/alcohol-based medium solution. As general leveling treatment, there is known addition of an additive, for example, a thickening agent or a defoaming agent. However, none of such additives can have the effect of the present invention.

The amount of the water/alcohol-based medium solution to be added onto the coating film on the inner surface of the vessel is from 15 mg/cm$^2$ to 250 mg/cm$^2$, preferably from 30 mg/cm$^2$ to 190 mg/cm$^2$. When the amount of the solution falls within the range of from 30 mg/cm$^2$ to 190 mg/cm$^2$, the solution can uniformly permeate the coating film to sufficiently swell the coating film, and thus the leveling treatment can be performed.

The water/alcohol-based medium solution in the step (B) may be any water/alcohol-based medium solution as long as the coating film formed in the step (A) can be subjected to the leveling treatment. An alcohol-based solvent contained in the water/alcohol-based medium solution is preferably a lower alcohol. Examples of the water/alcohol-based medium solution include: water and methanol; water and ethanol; water and 2-propanol; and a mixed solvent obtained by combining those mixed liquids. The ratio of water and the alcohol-based solvent only needs to be such that the coating film obtained in the step (A) can be subjected to the leveling treatment. However, in consideration of the evaporation rate, the following ratio is preferred: 10 wt % to 50 wt % of water and 50 wt % to 90 wt % of the alcohol-based solvent.

The method of manufacturing a vessel for embryoid body formation of the present invention preferably includes, after the step (A) and the step (B), a step (C) of sterilizing the inner surface of the vessel having the homogenized coating film. As means for the sterilizing, any sterilizing means may be used as long as the object of the present invention is not impaired. Examples thereof include sterilization treatment with an ethylene oxide gas (EOG), sterilization treatment with a γ-ray, and sterilization treatment with an electron beam. Of those, sterilization treatment with EOG is preferred to any other sterilization treatment in terms of suppression of cell adhesion.

The vessel for embryoid body formation of the present invention may have any shape as long as the vessel allows formation of a region for floating culture of stem cells. With regard to the shape of the vessel for embryoid body formation, a vessel having, for example, a flat bottom, a funnel-like V-bottom, or a hemispherical round bottom may be used. Of those, a flat bottom is preferred. As the vessel for embryoid body formation of the present invention, there are given existing cell culture vessels made of plastic, such as a cell culture dish, a cell culture multidish, a cell culture plate, a cell culture bag, and a cell culture flask. For obtaining an embryoid body of an appropriate size, the vessel is preferably a cell culture dish or a cell culture plate. As a material for the vessel for embryoid body formation, there are given polystyrene, polypropylene, polyethylene, and an acrylic resin.

A method of forming an embryoid body through use of a vessel for embryoid body formation for floating culture of stem cells to form an embryoid body of the present invention includes at least the following steps (D) and (E):

the step (D) of providing a vessel for embryoid body formation formed by: a step (A) of coating an inner surface of a vessel defining a region for floating culture of stem cells with an alcohol-based medium solution having mixed therein a compound having, in a side chain thereof, a phosphorylcholine-like group represented by the formula (1) so that the amount of the compound having, in the side chain thereof, the phosphorylcholine-like group is from 0.1 mg/cm$^2$ to 10 mg/cm$^2$, followed by drying; and a step (B) of adding, to a coating film on the inner surface of the vessel produced in the step (A), a water/alcohol-based medium solution at from 15 mg/cm$^2$ to 150 mg/cm$^2$ to swell the coating film, followed by drying; and the step (E) of subjecting embryonic stem cells to floating culture in the vessel for embryoid body formation provided in the step (D).

A known culture method may be used for the floating culture of stem cells using the vessel for embryoid body formation of the present invention. For example, the floating culture may be carried out by floating culturing undifferentiated stem cells that have been cultured on feeder cells, in the vessel for embryoid body formation by, for example, a known method under known conditions. In this case, the culture liquid in the vessel for embryoid body formation may be kept under static conditions or gently shaken.

The medium constituting the culture liquid may be a medium supplemented with fetal calf serum and various growth factors used for the related-art hanging drop method or the like. For example, Iscove's modified Dulbecco's medium (IMDM medium) supplemented with 20 vol % fetal calf serum and various growth factors, and Dulbecco's Modified Eagle medium (DMEM medium) supplemented with 10 vol % fetal calf serum and various growth factors may be used.

The concentration of the stem cells in the culture liquid may vary depending on the size, shape, or the like, of the vessel for embryoid body formation to be provided, but is usually from $1.0 \times 10^2$ cells/mL to $1.0 \times 10^6$ cells/mL. In particular, the concentration of the stem cells in the case of using a 96-well plate as the vessel for embryoid body formation is preferably from $1.0 \times 10^3$ cells/mL to $1.0 \times 10^5$ cells/mL in order to form embryoid bodies with good reproducibility.

EXAMPLES

Now, the present invention is described in more detail by way of Examples and Comparative Examples, but the present invention is not limited thereto.

First, in the following Synthesis Examples 1 to 4, synthesis examples of copolymers (1) to (4) each serving as a compound having, in a side chain thereof, a phosphorylcholine-like group are described.

Synthesis Example 1

35.7 g of MPC and 4.3 g of n-butyl methacrylate (BMA) (MPC/BMA=80/20 (by molar ratio)) were dissolved in 160 g of ethanol. The solution was placed in a four-neck flask, and bubbled with nitrogen for 30 minutes. After that, 0.82 g of azobisisobutyronitrile was added at 60° C., and the mixture was reacted for polymerization for 8 hours. The polymer liquid was added dropwise into 3 L of diethyl ether under stirring, and the resulting precipitate was recovered by filtration and vacuum dried at room temperature for 48 hours, to obtain 29.6 g of powder. The weight average molecular weight of the obtained powder measured by GPC under the following conditions was found to be 153,000. Compositional analysis by $^1$H-NMR revealed that MPC/BMA=80/20 (by molar ratio). The powder is designated as copolymer (1) of a phosphorylcholine-like group-containing monomer (M).

<Measurement Conditions of GPC>
(1) Sample: A sample was dissolved in a chloroform/methanol (6/4 (by volume)) mixed solvent containing 0.5 wt % lithium bromide to prepare a 0.5 wt % polymer solution. The amount of the sample solution used was 20 L.
(2) Column: Two PLgel 5 μm MIXED-C columns arranged in series (manufactured by Polymer Laboratories Ltd.) were used at a column temperature of 40° C., and a molecular weight calculating program with integrator (GPC program for SC-8020) manufactured by Tosoh Corporation was used.
(3) Eluting solvent: A chloroform/methanol (6/4 (vol %)) mixed solvent containing 0.5 wt % lithium bromide was used at a flow rate of 1.0 mL/min.
(4) Detection: Differential refractive index detector
(5) Reference material: Polymethyl methacrylate (PMMA) (manufactured by Polymer Laboratories Ltd.)

Synthesis Example 2

23.5 g of MPC and 26.5 g of n-butyl methacrylate (BMA) (MPC/BMA=30/70 (by molar ratio)) were dissolved in 75 g of ethanol. The solution was placed in a four-neck flask, and bubbled with nitrogen for 30 minutes. After that, 0.41 g of azobisisobutyronitrile was added at 55° C., and the mixture was reacted for polymerization for 24 hours. The polymer liquid was added dropwise into 3 L of diethyl ether under stirring, and the resulting precipitate was recovered by filtration and vacuum dried at room temperature for 48 hours, to obtain 32.0 g of powder. The weight average molecular weight measured by GPC in the same manner as in Synthesis Example 1 was found to be 353,000. Compositional analysis by $^1$H-NMR revealed that MPC/BMA=30/70 (by molar ratio). The powder is designated as copolymer (2).

Synthesis Example 3

38.0 g of MPC and 2.0 g of glycidyl methacrylate (GMA) (MPC/GMA=90/10 (by molar ratio)) were dissolved in 358 g of isopropanol. The solution was placed in a four-neck flask, and bubbled with nitrogen for 30 minutes. After that, 2.18 g of a toluene solution of 20 wt % t-butyl peroxypivalate was added at 60° C., and the mixture was reacted for polymerization for 5 hours. The polymer liquid was added dropwise into 3 L of diethyl ether under stirring, and the resulting precipitate was recovered by filtration and vacuum dried at room temperature for 4.8 hours, to obtain 28.4 g of powder. Compositional analysis by $^1$H-NMR revealed that MPC/GMA=90/10 (by molar ratio). The weight average molecular weight measured by GPC in the same manner as in Synthesis Example 1 was found to be 53,000. The powder is designated as copolymer (3).

Synthesis Example 4

25.9 g of MPC, 16.6 g of BMA, and 7.5 g of methacrylic acid (MA) (MPC/BMA/MA=30/40/30 (by molar ratio)) were dissolved in 75 g of n-propanol. The solution was placed in a four-neck flask, and bubbled with nitrogen for 30 minutes. After that, 2.18 g of a toluene solution of 20 wt % t-butyl peroxypivalate was added at 50° C., and the mixture was reacted for polymerization for 5 hours. The polymer liquid was added dropwise into 3 L of diethyl ether under stirring, and the resulting precipitate was recovered by filtration and vacuum dried at room temperature for 48 hours, to obtain 28.4 g of powder. Compositional analysis by $^1$H-NMR revealed that MPC/BMA/GMA=30/40/30 (by molar ratio). The weight average molecular weight measured by GPC in the same manner as in Synthesis Example 1 was found to be 108,000. The powder is designated as copolymer (4).

(Example 1) Production of Vessel for Embryoid Body Formation 0.5 g of the copolymer (1) synthesized in Synthesis Example 1 was dissolved in 100 mL of ethanol to prepare a copolymer solution. 0.03 mL of the copolymer solution was placed in each well (area per well: about 0.33 cm$^2$) of a tissue culture F-bottom 96-well plate made of polystyrene (manufactured by Nunc), followed by drying at room temperature overnight. Subsequently, a water/ethanol mixed solvent (weight ratio: 70/30) was added as a post-treatment liquid for leveling, followed by drying at room temperature overnight. The obtained F-bottom 96-well plate made of polystyrene was placed in a bag for sterilization, and then the vessel was subjected to sterilization with an ethylene oxide gas (sterilization with EOG) so as to satisfy a sterilization standard based on ISO 11135-1 (SAL<10$^{-6}$). Thus, a vessel for embryoid body formation was produced.

(Examples 2 to 6 and Comparative Examples 1 to 6) Production of Vessels for Embryoid Body Formation Vessels for embryoid body formation were produced in the same manner as in Example 1 except that the following conditions were changed as shown in Table 1 and Table 2.

First, the kind of the copolymer was changed. 0.5 g of the copolymer was weighed out and 100 mL of ethanol was added to prepare a copolymer solution. The addition amount of the copolymer solution was changed, and the copolymer solution was injected into each well of the tissue culture F-bottom 96-well plate made of polystyrene, followed by drying. Further, the kind of the post-treatment liquid for leveling was changed, and drying was performed at room temperature overnight. A vessel for embryoid body formation was produced without the addition of any post-treatment liquid for leveling (Comparative Example 3). In addition, sterilization was performed by sterilization with a γ-ray or sterilization with an electron beam as well as sterilization with EOG.

A suspension of 5×10$^3$ cells/mL of mouse stem cells prepared by a preparation method for a suspension of mouse stem cells described below was plated at 0.2 mL per well into each well of each of the vessels for embryoid body formation produced in Examples 1 to 6 and Comparative Examples 1 to 6. After culture under the conditions of 37° C. and 5% $CO_2$ for 5 days, the state of embryoid body formation was observed under a phase contrast microscope.

The results are shown in Table 1 and Table 2. In addition, a photocopy of a phase contrast micrograph of an embryoid body cultured through use of the vessel for embryoid body formation of Example 3 is shown in FIG. 1. In addition, a photocopy of a phase contrast micrograph of an embryoid body formed through use of the vessel for embryoid body formation of Comparative Example 3 is shown in FIG. 2.

In Table 1 and Table 2, a cell adhesion property was evaluated by quantitatively evaluating cells remaining in each well after removal of floating cells on the basis of the amount of formazan produced through use of a MTT reagent. A ratio of cell adhesion of less than 5% was defined as acceptable, and a ratio of cell adhesion of 5% or more was defined as unacceptable.

In addition, in Table 1 and Table 2, embryoid body formation was evaluated and indicated as: A when an embryoid body of a sufficient size for differentiation was formed; B when an embryoid body was formed but was not of a sufficient size or shape; and C when no embryoid body was formed.

As demonstrated in Examples 1 to 6, it has been found that when the step (A) of controlling the addition amount of the copolymer and the step (B) of performing leveling treatment are combined, an embryoid body of a sufficient size for differentiation is formed, and good observability under a microscope can be achieved without adhesion of cells to any of all the wells.

TABLE 1

|  |  | Example 1 | Example 2 | Example 3 | Example 4 | Example 5 | Example 6 |
| --- | --- | --- | --- | --- | --- | --- | --- |
| Step (A) | Copolymer | (1) | (1) | (2) | (2) | (3) | (4) |
|  | Addition amount per 1 cm$^2$ of inner surface of vessel | 0.5 mg | 2 mg | 4 mg | 10 mg | 4 mg | 4 mg |
| Step (B) | Solution | Ethanol/water (70/30; weight ratio) | Ethanol/water (80/20; weight ratio) | Ethanol/water (70/30; weight ratio) | Ethanol/water (50/50; weight ratio) | Ethanol/water (50/50; weight ratio) | Ethanol/water (50/50; weight ratio) |
|  | Addition amount (mg/well) | 25 mg | 30 mg | 25 mg | 150 mg | 40 mg | 40 mg |
| Step (C) |  | EOG | EOG | EOG | EOG | γ-ray | Electron beam |
| Cell adhesion |  | Acceptable (2%) | Acceptable (1%) | Acceptable (0%) | Acceptable (0%) | Acceptable (4%) | Acceptable (3%) |
| Embryoid body formation |  | A | A | A | A | A | A |
| Optical observation |  | ○ | ○ | ○ | ○ | ○ | ○ |

TABLE 2

|  |  | Comparative Example 1 | Comparative Example 2 | Comparative Example 3 | Comparative Example 4 | Comparative Example 5 | Comparative Example 6 |
| --- | --- | --- | --- | --- | --- | --- | --- |
| Step (A) | Copolymer | (1) | (2) | (1) | (2) | (2) | (2) |
|  | Addition amount per 1 cm of inner surface of vessel | 0.5 mg | 20 mg | 1 mg | 10 mg | 10 mg | 10 mg |
| Step (B) | Solution | Ethanol/water (70/30; weight ratio) | Ethanol/water (80/20; weight ratio) | None | 100% Ethanol | Ethanol/water (70/30; weight ratio) | Methanol/water (70/30; weight ratio) |
|  | Addition amount (mg/well) | 25 mg | 25 mg | — | 20 mg | 5 mg | 250 mg |
| Step (C) |  | EOG | EOG | EOG | γ-ray | γ-ray | Electron beam |
| Cell adhesion |  | Unacceptable (8%) | Acceptable (1%) | Acceptable (0%) | Acceptable (4%) | Acceptable (4%) | Acceptable (3%) |
| Embryoid body formation |  | C | B | A | A | B | B |
| Optical observation |  | ○ | x | x | x | x | x |

<Preparation Method for Suspension of Mouse Stem Cells>

(1) Culture of Feeder Cells

As feeder cells, SIM mouse fibroblasts (hereinafter abbreviated as "STO cells") were used. The STO cells were cultured in Dulbecco's modified Eagle's medium (hereinafter abbreviated as "DMEM medium", manufactured by Gibco) supplemented with 100 units/mL of penicillin, 100 µg/mL of streptomycin, and 10 vol % inactivated fetal calf serum (FCS). The cultured STO cells were treated with a 10 µg/mL mitomycin C solution (manufactured by Sigma) for 3 hours, and then the resultant was used as a cell suspension. The suspension of the STO cells was plated in a tissue culture 6-well multidish at $5 \times 10^5$ cells per well. The cells were cultured under the conditions of 37° C. and 5% $CO_2$ for 16 hours or more to prepare feeder cells.

(2) Culture of Mouse Stem Cells

As stem cells, 129SV mouse ES cells were used. The medium for the stem cells was a DMEM medium supplemented with 15% KnockOut (trade mark) serum replacement (KSR: manufactured by Gibco), 1 mM sodium pyruvate (manufactured by Gibco), 0.1 mM MEM non-Essential amino acids (manufactured by Gibco), 0.1 mM 2-mercaptoethanol (manufactured by Sigma), 100 units/mL of penicillin, 100 µg/mL of streptomycin, and 1,000 units/mL of murine leukemia inhibitory factor (mLIF: manufactured by Chemicon) (hereinafter abbreviated as "stem medium"). $2 \times 10^5$ cells/well of the stem cells were plated on the feeder cells prepared in paragraph (1) above. The mouse stem cells were cultured under the conditions of 37° C. and 5% $CO_2$ for 3 days.

The mouse stem cells cultured in paragraph (2) above were released by a common procedure using 0.1% trypsin-EDTA, and then suspended in an IMDM medium (manufactured by Gibco, without mLIF) supplemented with 15% fetal calf serum (manufactured by Gibco), 0.1 mM 2-mercaptoethanol (manufactured by Sigma), 100 units/mL of penicillin, and 100 µg/mL of streptomycin, to prepare a suspension of mouse stem cells at $5 \times 10^3$ cells/mL.

INDUSTRIAL APPLICABILITY

The method of manufacturing a vessel for embryoid body formation of the present invention can provide a vessel having a uniformized vessel surface, and being excellent in efficiency of embryoid body formation and excellent in optical observability as compared to a related-art vessel for embryoid body formation.

The invention claimed is:

1. A method of manufacturing a vessel suitable for improved optical observation of embryoid body formation for use in floating culture of stem cells to form an embryoid body, the method comprising:

a step (A) of coating an inner surface of a vessel defining a region for floating culture of stem cells with an alcohol-based medium solution having mixed therein a compound having, in a side chain thereof, a phosphorylcholine-like group represented by the formula (1) so that an amount of the compound having, in the side chain thereof, the phosphorylcholine-like group is from 0.1 mg/cm² to 10 mg/cm², followed by drying; and a step (B) of adding, to a coating film on the inner surface of the vessel produced in the step (A), a water and alcohol-based medium solution at from 15 mg/cm² to 150 mg/cm² to swell the coating film, and removing the water and alcohol by a step consisting of evaporating the medium solution followed by drying:

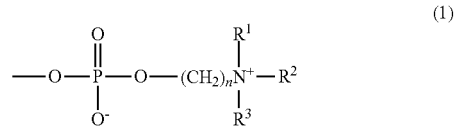

where $R^1$, $R^2$, and $R^3$ are identical or different groups, and each represent a hydrogen atom, or an alkyl group or hydroxyalkyl group having 1 to 6 carbon atoms, and n represents an integer of from 1 to 4, so as to manufacture a vessel which permits optical observation of embryoid body formation therein comprising a levelled inner surface coating which provides improved optical observation of embryoid body formation therein and which exhibits less than 5% stem cell adhesion.

2. A method of manufacturing a vessel for embryoid body formation according to claim 1, further comprising a step (C) of sterilizing the inner surface of the vessel with an ethylene oxide gas.

3. A method of manufacturing a vessel for embryoid body formation according to claim 1, wherein the compound having, in the side chain thereof, the phosphorylcholine-like group comprises at least one kind of a copolymer of a phosphorylcholine-like group-containing monomer (M) represented by the formula (2) and another monomer:

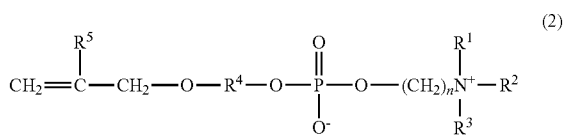

where $R^1$, $R^2$, and $R^3$ are identical or different groups, and each represent a hydrogen atom, or an alkyl group or hydroxyalkyl group having 1 to 6 carbon atoms, $R^4$ represents an alkyl group having 1 to 6 carbon atoms, $R^5$ represents a hydrogen atom or a methyl group, and n represents an integer of from 1 to 4.

4. A method of manufacturing a vessel for embryoid body formation according to claim 2, wherein the compound having, in the side chain thereof, the phosphorylcholine-like group comprises at least one kind of a copolymer of a phosphorylcholine-like group-containing monomer (M) represented by the formula (2) and another monomer:

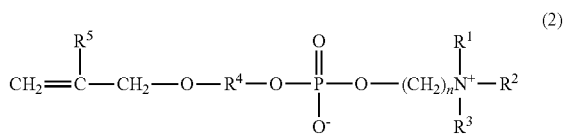

where $R^1$, $R^2$, and $R^3$ are identical or different groups, and each represent a hydrogen atom, or an alkyl group or hydroxyalkyl group having 1 to 6 carbon atoms, $R^4$ represents an alkyl group having 1 to 6 carbon atoms, $R^5$ represents a hydrogen atom or a methyl group, and n represents an integer of from 1 to 4.

5. A method of manufacturing a vessel for embryoid body formation according to claim 3, wherein the another monomer contains an alkyl (meth)acrylate or glycidyl (meth)acrylate.

6. A method of manufacturing a vessel for embryoid body formation according to claim 4, wherein the another monomer contains an alkyl (meth)acrylate or glycidyl (meth) acrylate.

7. A method of manufacturing a vessel for embryoid body formation according to claim 1, wherein the compound having, in the side chain thereof, the phosphorylcholine-like group comprises a copolymer of 2-methacryloyloxyethyl-phosphorylcholine, and butyl methacrylate, glycidyl methacrylate, and/or methacrylic acid.

8. A method of manufacturing a vessel for embryoid body formation according to claim 2, wherein the compound having, in the side chain thereof, the phosphorylcholine-like group comprises a copolymer of 2-methacryloyloxyethyl-phosphorylcholine, and butyl methacrylate, glycidyl methacrylate, and/or methacrylic acid.

9. A method of manufacturing a vessel for embryoid body formation according to claim 1, wherein the compound having, in the side chain thereof, the phosphorylcholine-like group comprises a copolymer of 2-methacryloyloxyethyl-phosphorylcholine and butyl methacrylate.

10. A method of manufacturing a vessel for embryoid body formation according to claim 2, wherein the compound having, in the side chain thereof, the phosphorylcholine-like group comprises a copolymer of 2-methacryloyloxyethyl-phosphorylcholine and butyl methacrylate.

11. A method of manufacturing a vessel for embryoid body formation according to claim 9, wherein the copolymer has a molar ratio of 2-methacryloyloxyethylphosphorylcholine and butyl methacrylate of from 10 to 90:from 90 to 10.

12. A method of manufacturing a vessel for embryoid body formation according to claim 10, wherein the copolymer has a molar ratio of 2-methacryloyloxyethylphosphorylcholine and butyl methacrylate of from 10 to 90:from 90 to 10.

13. A method of manufacturing a vessel for embryoid body formation according to claim 1, wherein the compound having, in the side chain thereof, the phosphorylcholine-like group comprises a copolymer of 2-methacryloyloxyethyl-phosphorylcholine, butyl methacrylate, and methacrylic acid.

14. A method of manufacturing a vessel for embryoid body formation according to claim 2, wherein the compound having, in the side chain thereof, the phosphorylcholine-like group comprises a copolymer of 2-methacryloyloxyethyl-phosphorylcholine, butyl methacrylate, and methacrylic acid.

15. A vessel for embryoid body formation, which is manufactured by the method of manufacturing a vessel for embryoid body formation of claim 1.

16. A vessel for embryoid body formation, which is manufactured by the method of manufacturing a vessel for embryoid body formation of claim 2.

17. A method of forming an embryoid body through use of a vessel for embryoid body formation for use in floating culture of stem cells to form an embryoid body, the method comprising:
   a step (D) of providing a vessel for embryoid body formation comprising a levelled inner surface coating which provides improved optical observation of embryoid body formation therein and which exhibits less than 5% stem cell adhesion formed by:
      a step (A) of coating an inner surface of a vessel defining a region for floating culture of stem cells with an alcohol-based medium solution having mixed therein a compound having, in a side chain thereof, a phosphorylcholine-like group represented by the formula (1) so that an amount of the compound having, in the side chain thereof, the phosphorylcholine-like group is from 0.1 mg/cm² to 10 mg/cm², followed by drying; and
      a step (B) of adding, to a coating film on the inner surface of the vessel produced in the step (A), a water and alcohol-based medium solution at from 15 mg/cm² to 150 mg/cm² to swell the coating film, and removing the water and alcohol by a step consisting of evaporating the medium solution followed by drying; and
   a step (E) of subjecting embryonic stem cells to floating culture in the vessel for embryoid body formation provided in the step (D):

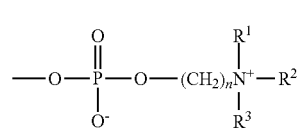

(1)

where $R^1$, $R^2$, and $R^3$ are identical or different groups, and each represent a hydrogen atom, or an alkyl group or hydroxyalkyl group having 1 to 6 carbon atoms, and n represents an integer of from 1 to 4.

18. A method of forming an embryoid body according to claim 17, further comprising, after the step (B), a step (C) of sterilizing the inner surface of the vessel with an ethylene oxide gas.

* * * * *